US010383823B2

(12) United States Patent
McGhee

(10) Patent No.: US 10,383,823 B2
(45) Date of Patent: *Aug. 20, 2019

(54) LIPOSOMAL CISPLATIN COMPOSITIONS FOR CANCER THERAPY

(71) Applicant: Mallinckrodt LLC, Hazelwood, MO (US)

(72) Inventor: William McGhee, Fenton, MO (US)

(73) Assignee: MALLINCKRODT LLC, Hazelwood, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/030,575

(22) Filed: Jul. 9, 2018

(65) Prior Publication Data

US 2018/0318219 A1    Nov. 8, 2018

Related U.S. Application Data

(63) Continuation of application No. 14/208,297, filed on Mar. 13, 2014, now Pat. No. 10,039,716.

(60) Provisional application No. 61/780,272, filed on Mar. 13, 2013.

(51) Int. Cl.
*A61K 33/24* (2019.01)
*A61K 9/127* (2006.01)

(52) U.S. Cl.
CPC ............ *A61K 9/1277* (2013.01); *A61K 9/127* (2013.01); *A61K 9/1272* (2013.01); *A61K 33/24* (2013.01)

(58) Field of Classification Search
CPC ..................................................... A61K 9/127
See application file for complete search history.

(56) References Cited

U.S. PATENT DOCUMENTS

| 5,843,473 A * | 12/1998 | Woodle ............... | A61K 9/1271 424/450 |
| 2004/0013720 A1* | 1/2004 | Ellens ................... | A61K 9/127 424/450 |
| 2006/0159739 A1* | 7/2006 | Lasic ................... | A61K 9/1271 424/450 |
| 2008/0193511 A1* | 8/2008 | Massing ................ | A61K 8/14 424/450 |
| 2014/0363491 A1* | 12/2014 | Okada ................. | A61K 9/1271 424/450 |

OTHER PUBLICATIONS

Trosko, J.E., et al in Nutation Research, 480-481, pp. 219-229, (2001).*

* cited by examiner

*Primary Examiner* — Gollamudi S Kishore
(74) *Attorney, Agent, or Firm* — Mayer Brown LLP

(57) ABSTRACT

The present invention provides a composition for the treatment of cancer including zwitterionic liposomes consisting essentially of: 50-65 mol % of a phosphatidylcholine lipid, 30-45 mol % of cholesterol, and 2-8 mol % of a PEG-lipid; and cisplatin. Cisplatin is encapsulated in the liposomes in an amount such that the ratio of the total lipid weight to the cisplatin weight is from about 65:1 to about 95:1. Methods for the preparation of liposomal cisplatin and the treatment of cancer are also disclosed.

17 Claims, 4 Drawing Sheets

Mean Growth of A427 Tumors in Nude Mice

1. Oblong and amorphous shape
(5 mole% DSPE-PEG2000)

2. Oblong liposome and few large Round particles
(10 mole %)

3. Rod-shaped, Small and large Round particles
(20 mole %)

4. More rod-shaped; small and large round particles,
(30 mole %)

1. Larger round liposome (5 mole% DSPE-PEG5000)

2. Rod-shaped and amorphous shape particles (10 mole %)

3. Amorphous particles, round particles, few liposomes (20 mole %)

4. Amorphous particle aggregates (30 mole %)

Mean Growth of A427 Tumors in Nude Mice

LIPOSOMAL CISPLATIN COMPOSITIONS FOR CANCER THERAPY

CROSS-REFERENCES TO RELATED APPLICATIONS

This application is a continuation of U.S. patent application Ser. No. 14/208,297, filed Mar. 13, 2014, which claims the benefit of priority to U.S. Provisional Application Ser. No. 61/780,272, filed Mar. 13, 2013, the content of which are incorporated herein by reference in their entirety to the full extent permitted by law.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Platinum-based drugs (or "platins") are effective anticancer drugs, forming DNA adducts that block DNA and RNA synthesis in cancer cells and inducing apoptosis. Cisplatin, carboplatin, and oxaliplatin are the main platins used for treating numerous solid tumors including ovarian, lung, colorectal, testicular, bladder, gastric, melanoma, and head and neck cancers. However, a major disadvantage of the platins is toxicity. Common side effects include kidney and nerve damage, high-end hearing loss, prolonged nausea, and vomiting.

Cisplatin (Cis-$PtCl_2(NH_3)_2$; shown below as Formula I) was approved by the FDA in 1978 for treatment of a variety of cancers and has been used since then for cancer treatment. Cisplatin exhibits a planar molecular structure, and has a solubility of about 1-2 mg/mL in 0.9% saline at 25-37° C. (8 mg/mL at 65° C.). Cisplatin is given to patients intravenously in saline (sodium chloride solution) and enters the cells by either passive diffusion or other facilitated transport mechanisms. Once inside the cytoplasm, cisplatin undergoes hydrolysis. The chloride ligands are each replaced by a molecule of water, producing a positively charged molecule. Uncharged species are unreactive, but monovalent cations and the divalent cationic species are most reactive.

Cisplatin is a particularly toxic drug. There are several disadvantages associated with use of the drug: a) its severe toxicity such as nephrotoxicity, neurotoxicity and emetogenesis, which is the main dose-limiting factor; b) its rapid excretion via kidneys resulting in a short circulation half life, c) its strong affinity to plasma proteins; and d) its limited aqueous solubility of about 1 mg/mL at room temperature. It is desirable to develop a formulation which will increase the concentration of cisplatin locally at the tumor site. It is also desirable to reduce the accumulation of cisplatin in other tissues to minimize the toxic side effects.

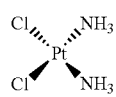
(I)

Liposomes have been used as delivery vehicles for platins in an attempt to reduce the drugs' toxicity. A liposome is a vesicle including a phospholipid bilayer separating exterior and interior aqueous phases. Liposomes are capable of carrying both hydrophobic drugs in the lipid bilayer and/or hydrophilic drugs in the aqueous core for drug delivery. Liposome size typically ranges from 50 to 250 nm in diameter, with diameters of 50 to 150 nm being particularly preferable for certain applications. The use of liposomal platins, including cisplatin, has presented considerable challenges. Liposomal platins demonstrate unique patterns of distribution, metabolism, and excretion from the body compared with the free drugs, as well as varying toxicity levels and unique side effects. In particular, optimizing the release rate of liposomal platins is a difficult balancing act between safety and efficacy. In general, leaky liposomes will make the encapsulated drugs more available, but cause more risk in toxicity similar to the native drugs. On the other hand, less leaky liposomes may reduce toxicity, but may not provide sufficient drug release for adequate efficacy.

U.S. Pat. No. 6,126,966 (the '966 patent) describes sterically-stabilized liposomal cisplatin. Specifically, the liposomal composition is described as of a vesicle-forming lipid (e.g., a phosphatidylcholine) with between 1-20 mole % of a vehicle-forming lipid derivative with a hydrophilic polymer having an uncharged cap (e.g., a poly(ethylene gycol)-modified phospholipid), said liposomes being formed such that the hydrophilic polymer forms a coating of hydrophilic polymer chains on both inner and outer surfaces of the liposomes. However, another report included cryo-TEM images of distearoylphosphatidylcholine (DSPC) dispersions containing a poly(ethylene glycol)-distearoylphosphatidylethanolamine (DSPE-PEG5000) at various concentrations (Biophysical Journal Volume 85, December 2003, pages 3839-3847). The images demonstrated mixtures containing as low as 7.1 mol % of DSPE-PEG5000 DSPC were predominantly micelles as opposed to the liposomes claimed in the '966 patent. Moreover, the sterically-stabilized liposomal cisplatin described in the '966 patent demonstrated limited in vivo efficacy in phase II study trials (Feng, et al. Cancer Chemother. Pharmacol. 54: 441-448. 2004). Clearly, liposome structure and physical properties, including in vivo half life and drug release profiles, can not be simply predicted based on the make-up of the liposomes.

Given the shortcomings of known formulations, it is desirable to develop liposomal cisplatin with improved properties compared to existing liposomal and non-liposomal platin therapeutics. There is a need for formulations that balance efficacy and safety and improve the bioavailability of cisplatin to targeted cancer cells. The present invention addresses these and other needs.

BRIEF SUMMARY OF THE INVENTION

In one aspect, the invention provides a composition for the treatment of cancer. The composition includes: (a) zwitterionic liposomes consisting essentially of 50-75 mol % of a phosphatidylcholine lipid or mixture of phosphatidylcholine lipids, 20-45 mol % of cholesterol, and 2-8 mol % of a PEG-lipid; and (b) cisplatin, encapsulated in the liposomes in an amount such that the ratio of the total lipid weight to the cisplatin weight is from about 40:1 to about 95:1.

In second aspect, the invention provides a composition for the treatment of cancer. The composition includes: (a) zwitterionic liposomes consisting essentially of 50-65 mol % of a phosphatidylcholine lipid or mixture of phosphatidylcholine lipids, 30-45 mol % of cholesterol, and 2-8 mol % of a PEG-lipid; and (b) cisplatin, encapsulated in the liposomes in an amount such that the ratio of the total lipid weight to the cisplatin weight is from about 65:1 to about 95:1.

In another aspect, the invention provides a method of treating cancer. The method includes administering to a subject in need thereof a composition of the invention.

DETAILED DESCRIPTION OF THE INVENTION

I. General

Figure 1:
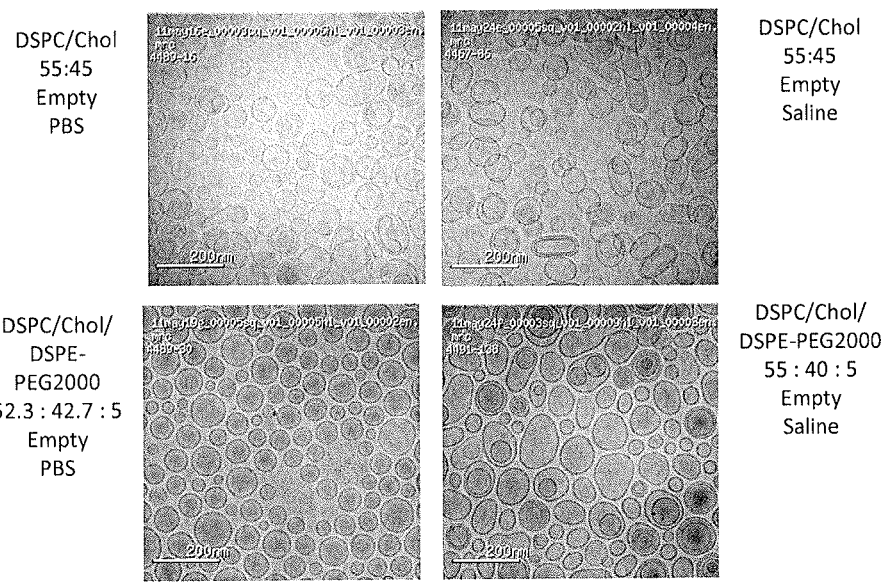
FIG. 1 shows TEM micrographs of liposomal cisplatin formulations with and without distearolyphosphatidylethanolamine-PEG2000 (DSPE-PEG2000).

The present invention relates to liposomal cisplatin compositions for cancer therapy. The liposome compositions described herein consist essentially of phosphatidylcholines, cholesterol, polyethylene glycol (PEG)-conjugated lipids, and encapsulated cisplatin. One of skill in the art will appreciate that the composition will often include an encapsulated medium or buffer, and an external medium. Methods for preparing the compositions and treatment of cancer with the compositions are also described. The compositions are particularly useful for enhancing intracellular cisplatin bioavailability in cancer cells and improving overall safety for cancer treatment. The compositions are broadly applicable for preventing and controlling cancers, providing a number of benefits to patients and clinicians.

II. Definitions

As used herein, the term "liposome" encompasses any compartment enclosed by a lipid bilayer. The term liposome includes unilamellar vesicles which are comprised of a single lipid bilayer and generally have a diameter in the range of about 20 to about 400 nm. Liposomes can also be multilamellar, which generally have a diameter in the range of 1 to 10 µm. In some embodiments, liposomes can include multilamellar vesicles (MLVs; from about 1 µm to about 10 µm in size), large unilamellar vesicles (LUVs; from a few hundred nanometers to about 10 µm in size), and small unilamellar vesicles (SUVs; from about 20 nm to about 200 nm in size).

As used herein, the term "zwitterionic liposome" refers to liposomes containing lipids with both positively- and negatively-charged functional groups in the same lipid molecule. The overall surface charge of a zwitterionic liposome will vary depending on the pH of the external medium. In general, the overall surface charge of a zwitterionic liposome is neutral or negative at physiological pH (i.e., pH~7.4).

As used herein, the terms "liposome size" and "average particle size" refer to the outer diameter of a liposome. Average particle size can be determined by a number of techniques including dynamic light scattering (DLS), quasi-elastic light scattering (QELS), and electron microscopy.

As used herein, the terms "molar percentage" and "mol %" refer to the number of moles of a given lipid component of a liposome divided by the total number of moles of all lipid components. Unless explicitly stated, the amounts of active agents, diluents, or other components are not included when calculating the mol % for a lipid component of a liposome.

As used herein, the term "phosphatidylcholine lipid" refers to a diacylglyceride phospholipid having a choline headgroup (i.e., a 1,2-diacyl-sn-glycero-3-phosphocholine). The acyl groups in a phosphatidylcholine lipid are generally derived from fatty acids having from 6-24 carbon atoms. The two acyl groups in a phosphatidylcholine lipid can have the same number of carbon atoms or different numbers of carbon atoms. Phosphatidylcholine lipids can include synthetic and naturally-derived 1,2-diacyl-sn-glycero-3-phosphocholines.

As used herein, the term "cholesterol" refers to 2,15-dimethyl-14-(1,5-dimethylhexyl)tetracyclo[8.7.0.0$^{2,7}$.-0$^{11,15}$]heptacos-7-en-5-ol (Chemical Abstracts Services Registry No. 57-88-5).

As used herein, the term "PEG-lipid" refers to a poly(ethylene glycol) polymer covalently bound to a hydrophobic or amphipilic lipid moiety. The lipid moiety can include fats, waxes, steroids, fat-soluble vitamins, monoglycerides, diglycerides, phospholipids, and sphingolipids. Preferred PEG-lipids include diacyl-phosphatidylethanolamine-N-[methoxy(polyethene glycol)]s and N-acyl-sphingosine-1-{succinyl[methoxy(polyethylene glycol)]}s. The molecular weight of the PEG in the PEG-lipid is generally from about 500 to about 5000 Daltons (Da; g/mol). The PEG in the PEG-lipid can have a linear or branched structure.

As used herein, the term "cisplatin" refers to (SP-4-2)-diamminedichloridoplatinum (II) (Chemical Abstracts Services Registry No. 15663-27-1).

As used herein, the term "composition" refers to a product comprising the specified ingredients in the specified amounts, as well as any product which results, directly or indirectly, from combination of the specified ingredients in the specified amounts. Pharmaceutical compositions of the present invention generally contain liposomal cisplatin as described herein and a pharmaceutically acceptable carrier, diluent, or excipient. By "pharmaceutically acceptable," it is meant that the carrier, diluent, or excipient must be compatible with the other ingredients of the formulation and non-deleterious to the recipient thereof.

As used herein, the term "alkanol" refers to a $C_{1-4}$ alkane having at least one hydroxy group. Alkanols include, but are not limited to, methanol, ethanol, isoproponal, and t-butanol.

As used herein, the term "porous filter" refers to a polymeric or inorganic membrane containing pores with a defined diameter (e.g., 30-1000 nm). Porous filters can be made of polymers including, but not limited to, polycarbonates and polyesters, as well as inorganic substrates including, but not limited to, porous alumina.

As used herein, the term "sterile filtering" refers to sterilization of a composition by passage of the composition through a filter with the ability to exclude microorganisms and/or viruses from the filtrate. In general, the filters used for sterilization contain pores that are large enough to allow passage of liposomes through the filter into the filtrate, but small enough to block the passage of organisms such as bacteria or fungi.

As used herein, the term "cancer" refers to conditions including human cancers and carcinomas, sarcomas, adenocarcinomas, lymphomas, leukemias, and solid and lymphoid cancers. Examples of different types of cancer include, but are not limited to, lung cancer (e.g., non-small cell lung cancer or NSCLC), ovarian cancer, prostate cancer, colorectal cancer, liver cancer (i.e., hepatocarcinoma), renal cancer (i.e., renal cell carcinoma), bladder cancer, breast cancer, thyroid cancer, pleural cancer, pancreatic cancer, uterine cancer, cervical cancer, testicular cancer, anal cancer, pancreatic cancer, bile duct cancer, gastrointestinal carcinoid tumors, esophageal cancer, gall bladder cancer, appendix cancer, small intestine cancer, stomach (gastric) cancer, cancer of the central nervous system, skin cancer, choriocarcinoma, head and neck cancer, blood cancer, osteogenic sarcoma, fibrosarcoma, neuroblastoma, glioma, melanoma, B-cell lymphoma, non-Hodgkin's lymphoma, Burkitt's lymphoma, Small Cell lymphoma, Large Cell lymphoma, monocytic leukemia, myelogenous leukemia, acute lymphocytic leukemia, acute myelocytic leukemia, and multiple myeloma.

As used herein, the terms "treat", "treating" and "treatment" refer to any indicia of success in the treatment or amelioration of a cancer or a symptom of cancer, including any objective or subjective parameter such as abatement; remission; diminishing of symptoms or making the cancer or cancer symptom more tolerable to the patient. The treatment or amelioration of symptoms can be based on any objective or subjective parameter, including, e.g., the result of a physical examination or clinical test.

As used herein, the terms "administer," "administered," or "administering" refer to methods of administering the liposome compositions of the present invention. The liposome compositions of the present invention can be administered in a variety of ways, including parenterally, intravenously, intradermally, intramuscularly, or intraperitoneally. The liposome compositions can also be administered as part of a composition or formulation.

As used herein, the term "subject" refers to any mammal, in particular a human, at any stage of life.

As used herein, the term "about" indicates a close range around a numerical value when used to modify that specific value. If "X" were the value, for example, "about X" would indicate a value from 0.9X to 1.1X, and more preferably, a value from 0.95X to 1.05X. Any reference to "about X" specifically indicates at least the values X, 0.9X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.1X.

III. Embodiments of the Invention

Liposomes

In one aspect, the invention provides a composition for the treatment of cancer. The composition includes: (a) zwitterionic liposomes consisting essentially of from about 50 mol % to about 75 mol % of a phosphatidylcholine lipid or mixture of phosphatidylcholine lipids, from about 20 mol % to about 45 mol % of cholesterol, and from about 2 mol % to about 8 mol % of a PEG-lipid; and (b) cisplatin, encapsulated in the liposome in an amount such that the ratio of the total lipid weight to the cisplatin weight is from about 40:1 to about 95:1.

In another aspect, the invention provides a composition for the treatment of cancer. The composition includes: (a) zwitterionic liposomes consisting essentially of from about 50 mol % to about 65 mol % of a phosphatidylcholine lipid or mixture of phosphatidylcholine lipids, from about 30 mol % to about 45 mol % of cholesterol, and from about 2 mol % to about 8 mol % of a PEG-lipid; and (b) cisplatin, encapsulated in the liposome in an amount such that the ratio of the total lipid weight to the cisplatin weight is from about 65:1 to about 95:1.

The liposomes of the present invention can contain any suitable phosphatidylcholine lipid (PC) or mixture of PCs. Suitable phosphatidylcholine lipids include saturated PCs and unsaturated PCs.

Examples of saturated PCs include 1,2-dilauroyl-sn-glycero-3-phosphocholine (DLPC), 1,2-dimyristoyl-sn-glycero-3-phosphocholine (dimyristoylphosphatidylcholine; DMPC), 1,2-distearoyl-sn-glycero-3-phosphocholine (distearoylphosphatidylcholine; DSPC), 1,2-dioleoyl-sn-glycero-3-phosphocholine (DOPC), 1,2-dipalmitoyl-sn-glycero-3-phosphocholine (dipalmitoylphosphatidylcholine; DPPC), 1-myristoyl-2-palmitoyl-sn-glycero-3-phosphocholine (MPPC), 1-palmitoyl-2-myristoyl-sn-glycero-3-phosphocholine (PMPC), 1-myristoyl-2-stearoyl-sn-glycero-3-phosphocholine (MSPC), 1-palmitoyl-2-stearoyl-sn-glycero-3-phosphocholine (PSPC), 1-stearoyl-2-palmitoyl-sn-glycero-3-phosphocholine (SPPC), and 1-stearoyl-2-myristoyl-sn-glycero-3-phosphocholine (SMPC).

Examples of unsaturated PCs include, but are not limited to, 1,2-dimyristoleoyl-sn-glycero-3-phosphocholine, 1,2-dimyristelaidoyl-sn-glycero-3-phosphocholine, 1,2-dipamiltoleoyl-sn-glycero-3-phosphocholine, 1,2-dipalmitelaidoyl-sn-glycero-3-phosphocholine, 1,2-dioleoyl-sn-glycero-3-phosphocholine (DOPC), 1,2-dielaidoyl-sn-glycero-3-phosphocholine, 1,2-dipetroselenoyl-sn-glycero-3-phosphocholine, 1,2-dilinoleoyl-sn-glycero-3-phosphocholine, 1-palmitoyl-2-oleoyl-sn-glycero-3-phosphocholine (palmitoyloleoylphosphatidylcholine; POPC), 1-palmitoyl-2-linoleoyl-sn-glycero-3-phosphocholine, 1-stearoyl-2-oleoyl-sn-glycero-3-phosphocholine (SOPC), 1-stearoyl-2-linoleoyl-sn-glycero-3-phosphocholine, 1-oleoyl-2-myristoyl-sn-glycero-3-phosphocholine (OMPC), 1-oleoyl-2-palmitoyl-sn-glycero-3-phosphocholine (OPPC), and 1-oleoyl-2-stearoyl-sn-glycero-3-phosphocholine (OSPC).

Lipid extracts, such as egg PC, heart extract, brain extract, liver extract, soy PC, and hydrogenated soy PC (HSPC) are also useful in the present invention.

In some embodiments, the phosphatidylcholine lipid is selected from POPC, DSPC, DMPC, and DPPC. In some embodiments, the phosphatidylcholine lipid is POPC. In some embodiments, the phosphatidylcholine lipid includes DSPC and DPPC.

In general, the compositions of the present invention include liposomes containing 50-75 mol % of a phosphatidylcholine lipid or mixture of phosphatidylcholine lipids. The liposomes can contain, for example, 50, 51, 52, 53, 54, 55, 56, 57, 58, 59, 60, 61, 62, 63, 64, 65, 66, 67, 68, 69, 70, 71, 72, 73, 74, or 75 mol % phosphatidylcholine. In some embodiments, the liposomes contain 50-55 mol % phosphatidylcholine. In general, the compositions of the present invention include liposomes containing 50-65 mol % of a phosphatidylcholine lipid or mixture of phosphatidylcholine lipids. In some embodiments, the liposomes contain 55-65 mol % phosphatidylcholine. In some embodiments, the liposomes contain 65-75 mol % phosphatidylcholine. In some embodiments, the liposomes contain about 75 mol % phosphatidylcholine. In some embodiments, the liposomes contain about 70 mol % phosphatidylcholine. In some embodiments, the liposomes contain about 65 mol % phosphatidylcholine. In some embodiments, the liposomes contain about 60 mol % phosphatidylcholine. In some embodiments, the liposomes contain about 55 mol % phosphatidylcholine.

The liposomes in the inventive compositions also contain 20-45 mol % of cholesterol (i.e., 2,15-dimethyl-14-(1,5-dimethylhexyl)tetracyclo[8.7.0.0$^{2,7}$.0$^{11,15}$]heptacos-7-en-5-ol). The liposomes can contain, for example, 20, 21, 22, 23, 24, 25, 26, 27, 28, 29, 30, 31, 32, 33, 34, 35, 36, 37, 38, 39, 40, 41, 42, 43, 44, or 45 mol % cholesterol. In some embodiments, the liposomes contain 20-30 mol % cholesterol. In some embodiments, the liposomes contain 30-40 mol % cholesterol. In some embodiments, the liposomes contain 30-45 mol % cholesterol. In some embodiments, the liposomes contain 40-45 mol % cholesterol. In some embodiments, the liposomes contain about 20 mol % cholesterol. In some embodiments, the liposomes contain about 25 mol % cholesterol. In some embodiments, the liposomes contain about 30 mol % cholesterol. In some embodiments, the liposomes contain about 35 mol % cholesterol. In some embodiments, the liposomes contain about 40 mol % cholesterol.

The liposomes of the present invention can include any suitable poly(ethylene glycol)-lipid derivative (PEG-lipid). In some embodiments, the PEG-lipid is selected from a diacyl-phosphatidylethanolamine-N-[methoxy(polyethene glycol)], an N-acyl-sphingosine-1-{succinyl[methoxy(polyethylene glycol)]}, and mixtures thereof. The molecular weight of the poly(ethylene glycol) in the PEG-lipid is generally in the range of from about 500 Da to about 5000 Da. The poly(ethylene glycol) can have a molecular weight of, for example, 750 Da, 1000 Da, 2000 Da, or 5000 Da. In some embodiments, the PEG-lipid is selected from distearoyl-phosphatidylethanolamine-N-[methoxy(polyethene glycol)-2000] (DSPE-PEG-2000) and distearoyl-phosphatidylethanolamine-N-[methoxy(polyethene glycol)-5000] (DSPE-PEG-5000). In some embodiments, the PEG-lipid is DSPE-PEG-2000.

In general, the compositions of the present invention include liposomes containing 2-8 mol % of the PEG-lipid. The liposomes can contain, for example, about 2, about 3, about 4, about 5, about 6, about 7, or about 8 mol % PEG-lipid. In some embodiments, the liposomes contain 4-6 mol % PEG-lipid. In some embodiments, the liposomes contain about 5 mol % PEG-lipid.

In some embodiments, the zwitterionic liposome includes about 55 mol % POPC, about 40 mol % cholesterol, and about 5 mol % DSPE-PEG(2000). In some embodiments, the zwitterionic liposome includes about 60 mol % POPC, about 35 mol % cholesterol, and about 5 mol % DSPE-PEG (2000). In some embodiments, the zwitterionic liposome includes about 65 mol % POPC, about 30 mol % cholesterol, and about 5 mol % DSPE-PEG(2000). In some embodiments, the zwitterionic liposome includes about 57 mol % POPC, about 38 mol % cholesterol, and about 5 mol % DSPE-PEG(2000).

In some embodiments, the zwitterionic liposome includes about 40-50 mol % DSPC, about 15-25 mol % DPPC, about 25-35 mol % cholesterol, and about 5 mol % DSPE-PEG (2000). In some embodiments, the zwitterionic liposome includes about 46 mol % DSPC, about 19 mol % DPPC, about 30 mol % cholesterol, and about 5 mol % DSPE-PEG (2000).

In some embodiments, the zwitterionic liposome includes about 55-75 mol % DSPC, about 20-40 mol % cholesterol, and about 2-8 mol % DSPE-PEG(2000). In some embodiments, the zwitterionic liposome includes about 55-75 mol % DSPC, about 20-40 mol % cholesterol, about 2-8 mol % DSPE-PEG(2000) and no DPPC. In some embodiments, the zwitterionic liposome includes about 65 mol % DSPC, about 30 mol % cholesterol, and 5 mol % DSPE-PEG(2000).

In some embodiments, the zwitterionic liposome includes about 45 mol % DSPC, about 20 mol % DPPC, about 30 mol % cholesterol, and about 5 mol % DSPE-PEG(2000). In some embodiments, the zwitterionic liposome includes about 46 mol % DSPC, about 19 mol % DPPC, about 30 mol % cholesterol, and about 5 mol % DSPE-PEG(2000).

In general, the compositions of the present invention contain liposome-encapsulated cisplatin in an amount such that a therapeutically effective dose of cisplatin can be delivered to a subject in a convenient dosage volume. The cisplatin content of a given formulation can be expressed as an absolution concentration (e.g., mg/mL) or as a relative amount with respect to the lipids in the liposomes. In general, the ratio of the total lipid weight to the cisplatin weight is from about 40:1 to about 95:1. In some embodiments, the ratio of the total lipid weight to the cisplatin weight is from about 65:1 to about 95:1. The lipid:cisplatin ratio can be, for example, 40:1, 45:1, 50:1, 55:1, 60:1, 65:1, 70:1, 75:1, 80:1, 85:1, 90:1, or 95:1. In some embodiments, the composition of the invention includes liposomes containing cisplatin encapsulated in the liposomes in an amount such that the ratio of the total lipid weight to the cisplatin weight is about 70:1. In some embodiments, the composition of the invention includes liposomes containing cisplatin encapsulated in the liposomes in an amount such that the ratio of the total lipid weight to the cisplatin weight is about 90:1.

Liposome size can be determined by a number of methods known to those of skill in the art. Liposome size can be determined, for example, by dynamic light scattering (DLS), quasi-elastic light scattering (QELS), analytical ultracentrifugation, or electron microscopy. In some embodiments, the compositions of the present invention include zwitterionic liposomes having an average particle size of from about 75 to about 125 nm (diameter, volume mean). For example, the liposomes can have a diameter of 75, 85, 90, 95, 100, 105, 110, 115, 120, or 125 nm. In some embodiments, the liposomes have an average particle size of 80-120 nm. In some embodiments, the liposomes have an average particle size of 90-120 nm. In some embodiments, the compositions of the invention contain liposomes have an average particle size of 90 nm (volume mean).

Methods for Preparing Liposomal Cisplatin

Liposomes can be prepared and loaded with cisplatin using a number of techniques that are known to those of skill in the art. Lipid vesicles can be prepared, for example, by hydrating a dried lipid film (prepared via evaporation of a mixture of the lipid and an organic solvent in a suitable vessel) with water or an aqueous buffer. Hydration of lipid films typically results in a suspension of multilamellar vesicles (MLVs). Alternatively, MLVs can be formed by diluting a solution of a lipid in a suitable solvent, such as a $C_{1-4}$ alkanol, with water or an aqueous buffer. Unilamellar vesicles can be formed from MLVs via sonication or extrusion through membranes with defined pore sizes. Encapsulation of cisplatin can be conducted by including the drug in the aqueous solution used for film hydration or lipid dilution during MLV formation. Cisplatin can also be encapsulated in pre-formed vesicles.

Accordingly, some embodiments of the invention provide a composition containing zwitterionic liposomes as described above, wherein the liposomes are prepared by a method including: a) forming a lipid solution containing the phosphatidylcholine lipid, the cholesterol, the PEG-lipid, and a solvent selected from a $C_{1-4}$ alkanol and a $C_{1-4}$ alkanol/water mixture; b) mixing the lipid solution with an aqueous buffer to form multilamellar vesicles (MLVs); c) extruding the MLVs through a porous filter to form small unilamellar vesicles (SUVs); and d) diafiltration to remove un-encapsulated cisplatin. In some embodiments, removal of unencapsulated cisplatin can also be performed by centrifugation. In some embodiments, encapsulation of the cisplatin is conducted by including the cisplatin in the aqueous buffer during formation of the MLVs. In some embodiments, liposome preparation further includes sterile filtering the zwitterionic liposomes.

Formulation and Administration

In some embodiments, the compositions of the invention can include a liposome as described above and a physiologically (i.e., pharmaceutically) acceptable carrier. The term "carrier" refers to a typically inert substance used as a diluent or vehicle for the liposomal cisplatin. The term also encompasses a typically inert substance that imparts cohesive qualities to the composition. Typically, the physiologically acceptable carriers are present in liquid form. Examples of liquid carriers include physiological saline, phosphate buffer, normal buffered saline (135-150 mM NaCl), water, buffered water, 0.4% saline, 0.3% glycine, 0.3M sucrose (and other carbohydrates), glycoproteins to provide enhanced stability (e.g., albumin, lipoprotein, globulin, etc.), and the like. Since physiologically acceptable carriers are determined in part by the particular composition being administered as well as by the particular method used to administer the composition, there are a wide variety of suitable formulations of pharmaceutical compositions of the present invention (See, e.g., Remington's Pharmaceutical Sciences, 17$^{th}$ ed., 1989).

The compositions of the present invention may be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate. Sugars can also be included for stabilizing the compositions, such as a stabilizer for lyophilized liposome compositions.

Formulations suitable for parenteral administration, such as, for example, by intraarticular, intravenous, intramuscular, intratumoral, intradermal, intraperitoneal, and subcutaneous routes, include aqueous and non-aqueous, isotonic sterile injection solutions. The injection solutions can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, such as lyophilized liposomes. In the practice of the present invention, compositions can be administered, for example, by intravenous infusion, intraperitoneally, intravesically, or intrathecally. Parenteral administration and intravenous administration are preferred methods of administration. The formulations of liposome compositions can be presented in unit-dose or multi-dose sealed containers, such as ampoules and vials.

The pharmaceutical preparation is preferably in unit dosage form. In such form the preparation is subdivided into unit doses containing appropriate quantities of the active component, e.g., a liposome composition. The unit dosage form can be a packaged preparation, the package containing discrete quantities of preparation. The composition can, if desired, also contain other compatible therapeutic agents.

Methods of Treating Cancer

In another aspect, the invention provides a method of treating cancer. The method includes administering to a subject in need thereof a composition containing liposomal cisplatin as described above. In some embodiments, the method includes administering a composition containing: (a) zwitterionic liposomes consisting essentially of from about 50 mol % to about 75 mol % of a phosphatidylcholine lipid or mixture of phosphatidylcholine lipids, from about 20 mol % to about 45 mol % of cholesterol, and from about 2 mol % to about 8 mol % of a PEG-lipid; and (b) cisplatin, encapsulated in the liposome in an amount such that the ratio of the total lipid weight to the cisplatin weight is from about 40:1 to about 95:1. In some embodiments, the method includes administering a composition containing: (a) zwitterionic liposomes consisting essentially of from about 50 mol % to about 65 mol % of a phosphatidylcholine lipid or mixture of phosphatidylcholine lipids, from about 30 mol % to about 45 mol % of cholesterol, and from about 2 mol % to about 8 mol % of a PEG-lipid; and (b) cisplatin, encapsulated in the liposome in an amount such that the ratio of the total lipid weight to the cisplatin weight is from about 65:1 to about 95:1. In some embodiments, the method includes administering a composition containing: a) zwitterionic liposomes consisting essentially of about 46 mol % DSPC, about 19 mol % DPPC; about 30 mol % cholesterol, and about 5 mol % DSPE-PEG(2000); and b) cisplatin, encapsulated in the liposome in an amount such that the ratio of the total lipid weight to the cisplatin weight is from about 40:1 to about 90:1. In some embodiments, the method includes administering a composition containing: a) zwitterionic liposomes consisting essentially of about 46 mol % DSPC, about 19 mol % DPPC; about 30 mol % cholesterol, and about 5 mol % DSPE-PEG(2000); and b) cisplatin, encapsulated in the liposome in an amount such that the ratio of the total lipid weight to the cisplatin weight is from about 70:1 to about 90:1. In some embodiments, the method includes administering a composition containing: a) zwitterionic liposomes consisting essentially of about 57 mol % POPC, about 38 mol % cholesterol, and about 5 mol % DSPE-PEG(2000); and b) cisplatin, encapsulated in the liposome in an amount such that the ratio of the total lipid weight to the cisplatin weight is from about 40:1 to about 90:1. In some embodiments, the method includes administering a composition containing: a) zwitterionic liposomes consisting essentially of about 57 mol % POPC, about 38 mol % cholesterol, and about 5 mol % DSPE-PEG(2000); and b) cisplatin, encapsulated in the liposome in an amount such that the ratio of the total lipid weight to the cisplatin weight is from about 70:1 to about 90:1. In some embodiments, the method includes administering a composition containing: a) zwitterionic liposomes consisting essentially of about 65 mol % DSPC, about 30 mol % cholesterol, and about 5 mol % DSPE-PEG(2000); and b) cisplatin, encapsulated in the liposome in an amount such that the ratio of the total lipid weight to the cisplatin weight is from about 40:1 to about 90:1.

In therapeutic use for the treatment of cancer, the liposome compositions of the present invention can be administered such that the initial dosage of cisplatin ranges from about 0.001 mg/kg to about 1000 mg/kg daily. A daily dose range of about 0.01-500 mg/kg, or about 0.1-200 mg/kg, or about 1-100 mg/kg, or about 10-50 mg/kg, or about 10 mg/kg, or about 5 mg/kg, or about 2 mg/kg, or about 1 mg/kg can be used.

The dosages may be varied depending upon the requirements of the patient, the severity of the cancer being treated, and the liposome composition being employed. For example, dosages can be empirically determined considering the type and stage of cancer diagnosed in a particular patient. The dose administered to a patient should be sufficient to affect a beneficial therapeutic response in the patient over time. The size of the dose will also be determined by the existence, nature, and extent of any adverse side-effects that accompany the administration of a particular liposome composition in a particular patient. Determination of the proper dosage for a particular situation is within the skill of the practitioner. Generally, treatment is initiated with smaller dosages which are less than the optimum dose of the liposome composition. Thereafter, the dosage is increased by small increments until the optimum effect under circumstances is reached. For convenience, the total daily dosage may be divided and administered in portions during the day, if desired.

The compositions may be administered alone in the methods of the invention, or in combination with other therapeutic agents. The additional agents can be anticancer agents or cytotoxic agents including, but not limited to, avastin, doxorubicin, oxaliplatin, carboplatin, 5-fluorouracil, gemcitabine or taxanes, such as paclitaxel and docetaxel. Additional anti-cancer agents can include, but are not limited to, 20-epi-1,25 dihydroxyvitamin D3,4-ipomeanol, 5-ethynyluracil, 9-dihydrotaxol, abiraterone, acivicin, aclarubicin, acodazole hydrochloride, acronine, acylfulvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, anastrozole, andrographolide, angiogenesis inhibitors, antagonist D, antagonist G, antarelix, anthramycin, anti-dorsalizing morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisaziridinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, capecitabine, caracemide, carbetimer, carboplatin, carboxamide-amino-triazole, carboxyamidotriazole, carest M3, carmustine, cam 700, cartilage derived inhibitor, carubicin hydrochloride, carzelesin, casein kinase inhibitors, castanospermine, cecropin B, cedefingol, cetrorelix, chlorambucil, chlorins, chloroquinoxaline sulfonamide, cicaprost, cirolemycin, cisplatin, cis-porphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cyclophosphamide, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, diethylnorspermine, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocarmycin SA, ebselen, ecomustine, edatrexate, edelfosine, edrecolomab, eflornithine, eflornithine hydrochloride, elemene, elsamitrucin, emitefur, enloplatin, enpromate, epipropidine, epirubicin, epirubicin hydrochloride, epristeride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, fluorocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, hereguline, hexamethylene bisacetamide, hydroxyurea, hypericin, ibandronic acid, idarubicin, idarubicin hydrochloride, idoxifene, idramantone, ifosfamide, ilmofosine, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatin, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide 7, lobaplatin, lombricine, lometrexol, lometrexol sodium, lomustine, lonidamine, losoxantrone, losoxantrone hydrochloride, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C inhibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, 06-benzylguanine, octreotide, okicenone, oligonucleotides, onapristone, ondansetron, oracin, oral cytokine inducer, ormaplatin, osaterone, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazofurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RII retinamide, RNAi, rogletimide, rohitukine, romurtide, roquinimex, rubiginone B1, ruboxyl, safingol, safingol hydrochloride, saintopin, sarcnu, sarcophytol A, sargramostim, SDI 1 mimetics, semustine, senescence derived inhibitor 1, sense oligonucleotides, signal transduction inhibitors, signal transduction modulators, simtrazene, single chain antigen binding protein, sizofuran, sobuzoxane, sodium borocaptate, sodium phenylacetate, solverol, somatomedin binding protein, sonermin, sparfosate sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine, vinorelbine tartrate, vinrosidine sulfate, vinxaltine, vinzolidine sulfate, vitaxin, vorozole, zanoterone, zeniplatin, zilascorb, zinostatin, zinostatin stimalamer, or zorubicin hydrochloride. In some embodiments, the method can include administration of a drug selected from fluorouracil, leucovorin, and mixtures thereof.

IV. Examples

Example 1. General Methods for Preparation of Liposomal Cisplatin Compositions

Encapsulation of cisplatin in liposome was carried out by solvent dilution method. Lipid mixtures (500 mg portions of varying lipid ratios) were dissolved in 1 mL t-BuOH/EtOH (1/1, v/v ratio), or t-BuOH/EtOH/water (49/49/2 v/v ratio), and heated at 70° C. until clear. 90 mg cisplatin was dissolved in 9 mL of buffer (145 mM NaCl, 10 mM histidine buffer pH 6.5) at 70° C.). The lipid solution was added to the cisplatin solution with rapid mixing to form multilamellar vesicles (MLVs). The MLVs were passed through two stacked 80 nm polycarbonate filters using a LIPEX™ Extruder (Northern Lipid Inc.) heated to 70° C. The vesicle size and size distributions were determined by using a particle size analyzer based on quasi elastic light scattering principle (QELS) following each pass, and the extrusion was stopped after a mean volume diameter of 90-120 nm was achieved. Following extrusion, the liposomes were diluted 10-fold with cold (2-15° C.) 145 mM NaCl. This step reduces the cisplatin concentration, and prevents formation of cisplatin precipitates. In addition, it reduces the solvent concentration, which might otherwise facilitate the release of cisplatin from the vesicles.

Diafiltration (also known as cross-flow filtration) was carried out with a Spectrum Laboratories cartridge (500 kD, 145 cm$^2$ surface area, Cat # X3-500-300-02N). It was used to remove unencapsulated cisplatin and residual organic solvents, exchange the external buffer, and concentrate the liposomes. Typically, the formulations underwent ultrafiltration to achieve a lipid concentration of 50 mg/mL, and subsequently diafiltered against 10 wash volumes of the indicated buffer followed by ultrafiltration to 70-90 mg/mL lipid and approximately 1 mg/mL cisplatin. Sterile filtration of the preparations was carried out with Sartorius 0.2 μm syringe filters with cellulose acetate membranes (Cat #16534-K, ~28 mm diameter, 6.2 cm$^2$ surface area) using thumb pressure. Drug formulations were filled into sterile depyrogenated vials and stored at 2-8° C.

Example 2. Liposome Morphology Varies with PEGylated Lipid Content

A series of liposomes containing DSPC, cholesterol, and DSPE-PEG(2000, or 5000) were prepared. The ratio of DSPC/Cholesterol was fixed at 55/45 (mole %), and the PEGylated lipids were 0, 5, 10, 20, 30 mole % of the total lipid compositions respectively. The liposome compositions are shown in Table 1. The cryo-TEM images are shown in the following FIGS. 1, 2, and 3. These images clearly indicate that the liposome morphology varies with the level of PEGylated lipid in the liposome. Beyond about 5 mole %, essentially, liposomes were unstable and large disk-shape particles were formed. Levels greater than 7 mole % led to particularly high morphological heterogeneity.

TABLE 1

Liposome Compositions for Morphological Study by Cryo-TEM

Figure 2:
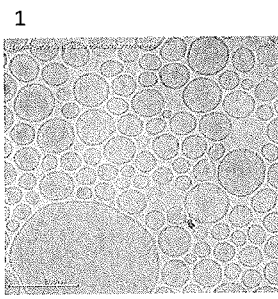
FIG. 2 shows TEM micrographs of liposomal cisplatin formulations containing varying amounts of DSPE-PEG2000.
Figure 2:
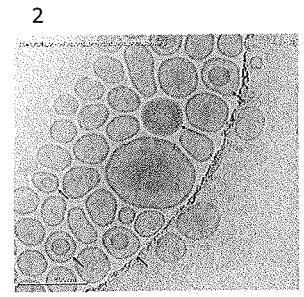
Figure 2:
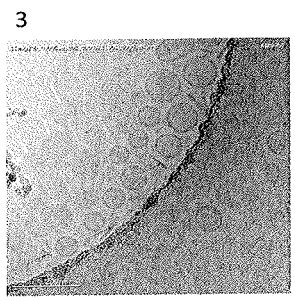
Figure 2:
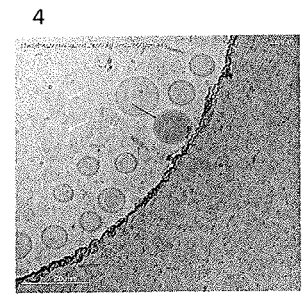
Figure 3:
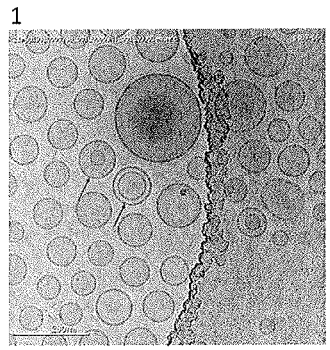
FIG. 3 shows TEM micrographs of liposomal cisplatin formulations containing varying amounts of DSPE-PEG5000.
Figure 3:
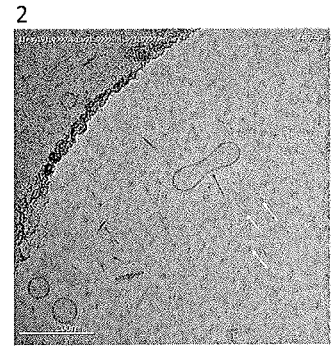
Figure 3:
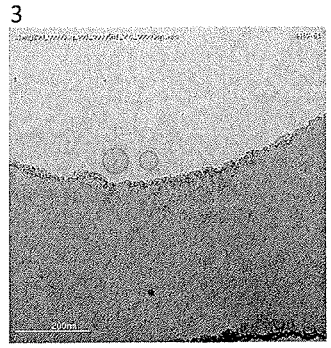
Figure 3:
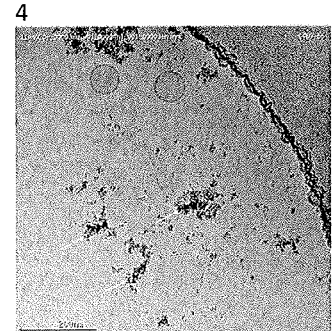

| DSPC Mole % | Cholesterol Mole % | DSPE-PEG (2000, 5000) Mole % | TEM Images |
|---|---|---|---|
| 55 | 45 | 0 | FIG. 1 |
| 55 | 40 | 5 | FIG. 1 (PEG2000), |
| 52.25 | 42.75 | 5 | FIG. 1 (PEG 2000), 2 (PEG2000), 3 (PEG 5000) |
| 49.5 | 40.5 | 10 | FIG. 2 (PEG 2000), FIG. 3 (PEG 5000) |
| 44.0 | 36 | 20 | FIG. 2 (PEG 2000), FIG. 3 (PEG 5000) |
| 38.5 | 31.5 | 30 | FIG. 2 (PEG 2000), FIG. 3 (PEG 5000) |

Example 3. Preparation of Liposomes with Various Phospholipids

A series of 14 liposome samples were prepared according to the method described above. The liposome compositions are listed in Table 2. For comparison purposes, Sample 1 was prepared according to Example 5 in U.S. Pat. No. 6,126,966 (SPI-077 composition). Samples 3, 4, 14 and 10 were prepared using DSPC phospholipids with cholesterol levels that ranged from 0 mole % to 40 mole %. Binary mixtures of DSPC and DPPC were used in Samples 5-9. Samples 5, 6, and 7 had higher cholesterol levels (30-40 mole %), and Samples 8-9 had lower cholesterol levels (10-20 mole %). Sample 10 was prepared using DSPC as the main phospholipid component for specific comparison with Samples 1 and 2, in which HSPC was used. Samples 11 and 12 were prepared using DPPC and DMPC as the main phospholipid components, in which DMPC has a fatty acid chain of 14 carbon atoms. Sample 13 used POPC as the main phospholipid component, in which the fatty acid chains contains saturated and unsaturated fatty acid.

TABLE 2

Liposome Compositions.

| Sample No. | Liposome Components | Mole Ratios, mole % |
|---|---|---|
| 1 | HSPC/Chol/DSPE-PEG(2000) | 51/44/5 |
| 2 | HSPC/Chol/DSPE-PEG(2000) | 55/40/5 |
| 3 | DSPC/Chol/DSPE-PEG(2000) | 95/0/5 |
| 4 | DSPC/Chol/DSPE-PEG(2000) | 75/20/5 |
| 5 | DSPC/DPPC/Chol/DSPE-PEG(2000) | 18.75/46.25/30/5 |
| 6 | DSPC/DPPC/Chol/DSPE-PEG(2000) | 27.5/27.5/40/5 |
| 7 | DSPC/DPPC/Chol/DSPE-PEG(2000) | 46.25/18.75/30/5 |
| 8 | DSPC/DPPC/Chol/DSPE-PEG(2000) | 65/10/20/5 |
| 9 | DSPC/DPPC/Chol/DSPE-PEG(2000) | 66.25/18.75/10/5 |
| 10 | DSPC/Chol/DSPE-PEG(2000) | 55/40/5 |
| 11 | DPPC/Chol/DSPE-PEG(2000) | 56.3/38.4/5.3 |
| 12 | DMPC/Chol/DSPE-PEG(2000) | 56.3/38.4/5.3 |
| 13 | POPC/Chol/DSPE-PEG(2000) | 56.3/38.4/5.3 |
| 14 | DSPC/Chol/DSPE-PEG(2000) | 65/30/5 |

Example 4. Safety and Efficacy of Liposomal Cisplatin Formulations

This example illustrates the superior efficacy and safety of Samples 7, 13, and 14 among the liposome compositions given in Table 2 in Example 2.

Liposome formulations were evaluated for PK studies in KB tumored animals. The animal study was carried out according to the following protocol. KB tumors were injected into nude mice and allowed to grow for ~10 days. 18 animals were injected with liposome preparations. Animals were sacrificed in groups of 3 at pre-treatment, 5 min, 4 hrs, 24 hrs, 48 hrs, and 96 hrs time points. Tissue samples were collected, and Pt/DNA adducts in tumors were analyzed. The possibility of Pt/DNA adducts generated ex vivo during sample analysis was evaluated using naive tumors spiked with cisplatin.

DNA from tissues was isolated via a procedure adapted from Qiagen's DNeasy protocol. Elution fractions were collected for DNA/Pt adduct Pt analysis. Pt quantification was determined by inductively-couple mass spectrometry (ICPMS) and DNA quantification was determined by the Picogreen fluorescence method.

Figure 4:
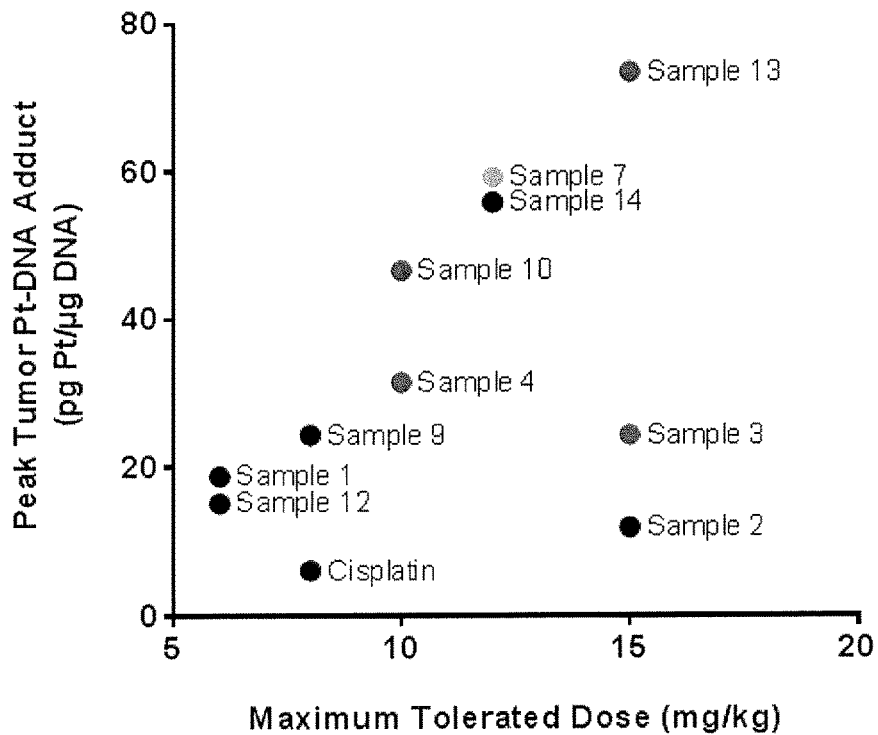
FIG. 4 shows the maximum tolerated dose (MTD) and DNA/Pt adduct levels resulting from administration of various liposomal cisplatin formulations in a mouse KB tumor model.
Figure 5:
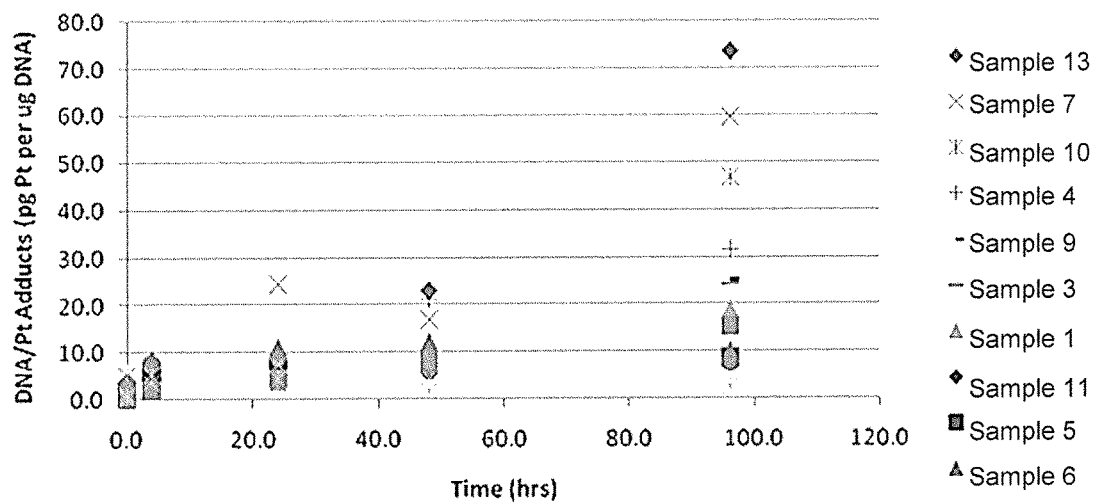
FIG. 5 shows the formation of DNA/Pt adducts in a mouse KB tumor model over time.

Liposome Samples 1-14 from Example 2 were used in vivo animal study according to the protocols described above. All formulations were dosed at 8 mg/kg cisplatin in the DNA/Pt Adduct assay. The values of peak tumor DNA/Pt adduct, measured by picogram (pg) Pt per microgram (ug) DNA, and maximum tolerated dose (MTD) were plotted as shown in in FIG. 4. The higher levels of DNA/Pt adduct and higher MTD values indicate better efficacy and safety for the respective liposome compositions. The DNA/Pt adduct values as a function of time is shown in FIG. 5. Sample 7 was evaluated in a tumor efficacy study with mice bearing A427 Lung xenograft tumors.

Samples 7, 13, and 14 clearly stand out in comparison with other samples. It should be noted Sample 1 exhibits a very low MTD, less than 8 mg/kg, and a peak DNA/Pt adduct value less than 20 pg of Pt/μg of DNA. Sample 7, 13 and 14 are clearly superior to Sample 1, an example described in U.S. Pat. No. 6,126,966. Furthermore, when native cisplatin was used, its MTD was less than 10 mg/kg, and DNA/Pt adduct values was less than 10 pg Pt per μg DNA.

Sample 7 stands out when comparing with Sample 5, 6, 8, 9 and 11. Sample 7 has a cholesterol level of 30 mol % and a binary mixture of DSPC/DPPC with the molar ratio greater than two fold. This trend is further supported by Sample 14, in which the composition has high cholesterol level of 30 mol %, but no DPPC, and better than Sample 11 in which DPPC was used alone without DSPC. Sample 5 has a 30 mol % cholesterol like samples 7 and 14, however, sample 5 contains only 18.75% DSPC with 46.25% DPPC and produced a lower DNA/Pt adduct.

In FIG. 5, Samples 7, 13, and 14 clearly stand out for their ability to form DNA/Pt adducts in vivo as a function of time. It should be noted that Sample 1 exhibits a peak DNA/Pt adduct value less than 20 pg Pt/μg DNA.

Figure 6:
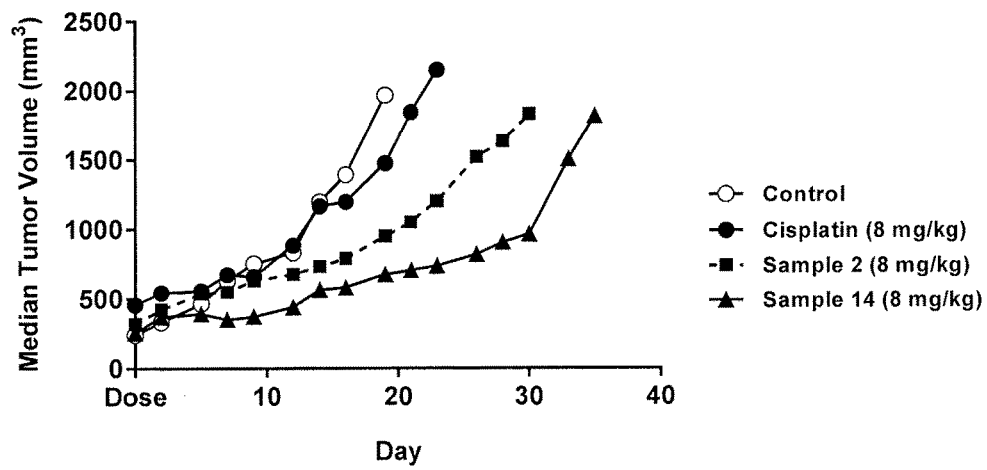
FIG. 6 shows median growth of KB tumors in nude mice over time after administration of liposomal cisplatin formulations.
Figure 7:
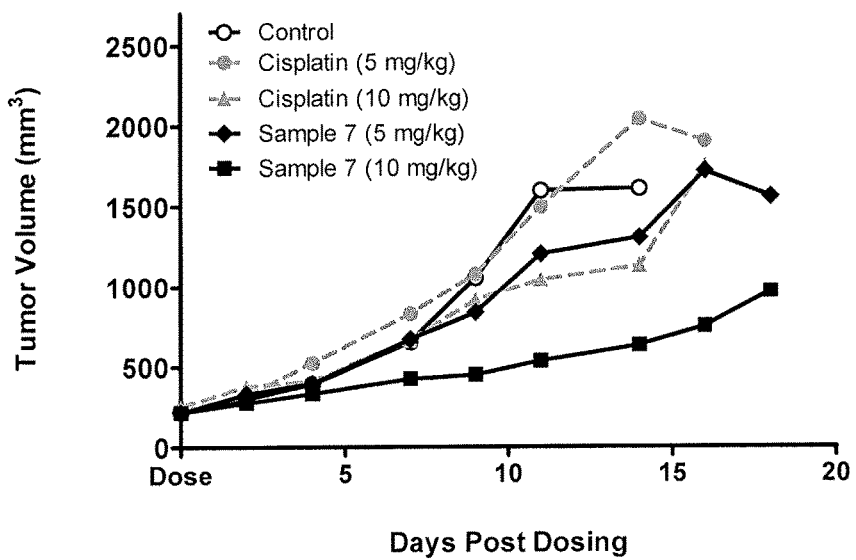
FIG. 7 shows the mean growth of A427 tumors in nude mice over time after administration of liposomal cisplatin formulations.

Efficacy was studied in a KB human model. Experiments were conducted as described for the KB model above. FIG. 6 shows that Sample 14 produced greater efficacy in vivo than cisplatin or Sample 2 (HSPC comparator) dosed at equivalent cisplatin levels in mice bearing KB human xenografts.

Efficacy was also studied in a A427 human NSCLC model. The experiments were conducted as described for the KB model above. FIG. 6 shows that Sample 7 has greater in vivo efficacy than cisplatin dosed at equivalent cisplatin levels in mice bearing A427 human NSCLC xenografts. A single treatment with Sample 7 resulted in tumor growth inhibition of 61%, 14 days post injection compared to 30% for free cisplatin.

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A method of treating cancer in a subject in need thereof comprising:
    administering to the subject a composition comprising:
    (a) zwitterionic liposomes consisting essentially of from about 55 mol % to about 65 mol % of a phosphatidylcholine lipid or mixture of phosphatidylcholine lipids, from about 30 mol % to about 45 mol % of cholesterol, and from about 2 mol % to about 5 mol % of a PEG-lipid; and
    (b) cisplatin, encapsulated in said liposome in an amount such that the ratio of the total lipid weight to the cisplatin weight is from about 65:1 to about 95:1;
    wherein the composition has a maximum tolerated dose greater than about 10 mg/kg and a peak DNA/platinum (Pt) adduct value greater than about 10 pg of Pt per μg of DNA, and
    wherein the cancer is carcinoma.

2. The method of claim 1, wherein the phosphatidylcholine lipid in the composition is selected from the group consisting of palmitoyloleoylphosphatidylcholine (POPC), distearoylphosphatidylcholine (DSPC), dimyristoylphosphatidylcholine (DMPC) and dipalmitoylphosphatidylcholine (DPPC).

3. The method of claim 1, wherein the phosphatidylcholine lipid in the composition is POPC.

4. The method of claim 1, wherein the phosphatidylcholine lipid in the composition comprises DSPC and DPPC.

5. The method of claim 1, wherein the phosphatidylcholine lipid in the composition is DSPC.

6. The method of claim 1, wherein the PEG-lipid in the composition is selected from the group consisting of a diacyl-phosphatidylethanolamine-N-[methoxy(polyethene glycol)], an N-acyl-sphingosine-1-{succinyl[methoxy(polyethylene glycol)]}, and mixtures thereof.

7. The method of claim 1, wherein the PEG-lipid in the composition is selected from the group consisting of distearoyl-phosphatidylethanolamine-N-[methoxy(polyethene glycol)-2000] (DSPE-PEG-2000) and distearoyl-phosphatidylethanolamine-N-[methoxy(polyethene glycol)-5000] (DSPE-PEG-5000).

8. The method of claim 1, wherein the zwitterionic liposome in the composition comprises about 40-50 mol % DSPC, about 15-25 mol % DPPC, about 25-35 mol % cholesterol, and about 5 mol % DSPE-PEG(2000).

9. The method of claim 1, wherein the zwitterionic liposome in the composition comprises about 46 mol % DSPC, about 19 mol % DPPC, about 30 mol % cholesterol, and about 5 mol % DSPE-PEG(2000).

10. The method of claim 1, wherein the zwitterionic liposome in the composition comprises about 55-75 mol % DSPC, about 20-40 mol % cholesterol, and about 5 mol % DSPE-PEG(2000).

11. The method of claim 1, wherein the zwitterionic liposome in the composition comprises about 65 mol % DSPC, about 30 mol % cholesterol, and about 5 mol % DSPE-PEG(2000).

12. The method of claim 1, wherein the zwitterionic liposome in the composition comprises about 57 mol % POPC, about 38 mol % cholesterol, and about 5 mol % DSPE-PEG(2000).

13. The method of claim 1, wherein the ratio of the total lipid weight to the cisplatin weight in the composition is about 75:1 to 90:1.

14. The method of claim 1, wherein the ratio of the total lipid weight to the cisplatin weight in the composition is about 90:1.

15. The method of claim 1, wherein the zwitterionic liposomes in the composition have an average particle size of from about 75 to about 125 nm (volume mean).

16. The method of claim 1, wherein the zwitterionic liposomes in the composition have an average particle size of about 90 nm (volume mean).

17. The method of claim 1, wherein the composition has greater efficacy in vivo than cisplatin to reduce mean tumor volume.

* * * * *